United States Patent
Ageland et al.

(12)

(10) Patent No.: US 6,559,284 B1
(45) Date of Patent: May 6, 2003

(54) PROCESS FOR PURIFYING A PROTEIN

(75) Inventors: Hans Ageland, Bromma (SE); Lena Nyström, Stockholm (SE); Josefine Persson, Lund (SE); Folke Tjerneld, Malmö (SE)

(73) Assignee: Esperion Therapeutics, Inc., Ann Arbor, MI (US)

( * ) Notice: Subject to any disclaimer, the term of this patent is extended or adjusted under 35 U.S.C. 154(b) by 1 day.

(21) Appl. No.: 08/924,994

(22) Filed: Sep. 5, 1997

Related U.S. Application Data

(60) Provisional application No. 60/026,740, filed on Sep. 26, 1996.

(30) Foreign Application Priority Data

Sep. 11, 1996 (SE) ................................................ 9603303

(51) Int. Cl.$^7$ ............................ C07K 1/14; C07K 14/00
(52) U.S. Cl. ...................... 530/359; 530/412; 530/421; 530/422; 530/424
(58) Field of Search ............................... 530/412, 421, 530/422, 424, 359

(56) References Cited

U.S. PATENT DOCUMENTS

| | | | |
|---|---|---|---|
| 4,740,304 A | | 4/1988 | Tjerneld et al. |
| 5,059,528 A | | 10/1991 | Bollen et al. |
| 5,089,602 A | | 2/1992 | Isliker et al. |
| 5,128,318 A | | 7/1992 | Levine et al. |
| 5,834,596 A | * | 11/1998 | Ageland et al. ............ 530/359 |
| 6,107,467 A | * | 8/2000 | Ageland et al. ............ 530/359 |

FOREIGN PATENT DOCUMENTS

| | | | |
|---|---|---|---|
| EP | 0262651 | | 4/1988 |
| EP | 267 703 | | 5/1988 |
| EP | 0308336 | | 3/1989 |
| EP | 333 474 | | 9/1989 |
| EP | 345 155 | | 12/1989 |
| EP | 345 615 | | 12/1989 |
| EP | 494 848 | | 7/1992 |
| JP | 61-96998 | | 5/1986 |
| JP | 01-95798 | | 4/1989 |
| JP | 06-228319 | | 8/1994 |
| JP | 8003198 | | 3/1996 |
| WO | WO8803166 | | 5/1988 |
| WO | WO9012879 | | 11/1990 |
| WO | WO 91/06655 | | 5/1991 |
| WO | WO9312143 | | 6/1993 |
| WO | WO9325581 | | 12/1993 |
| WO | WO9413819 | | 6/1994 |
| WO | WO 96/00237 | | 1/1996 |
| WO | WO96/04556 | * | 2/1996 |
| WO | WO9604556 | | 2/1996 |
| WO | WO9627608 | | 9/1996 |

OTHER PUBLICATIONS

Harris et al. 'Enzyme Purification Using Temperature Induced Phase Formation', Bioseparation vol. 2, pp. 237–246, 1991.*

Calabresi et al. 'Molecular Characterization Of Native And Recombinant Apolipoprotein A–I Milano Dimer', J. of Biol. Chem. vol. 269, No. 23, pp. 32168–32174, Dec. 23, 1994.*

Database Caplus on STN. No. 1995:421793. Soma et al. 'Recombinant Apolipoprotein A–Imilano Dimer Inhibits Carotid Intimal Thickening Induced By Pervascular Manipulation In Rabbits', Circ. Res. vol. 76, No. 3, pp. 405–411, 1995.*

Anspach, et al., "Removal of endotoxins by affinity sorbents," *J Chromatogr A* 711(1):81–92 (1995).

Badimon, et al., "Regression of atherosclerotic lesions by high density lipoprotein plasma fraction in the cholesterol–fed rabbit," *J. Clin Invest* 85(4):1234–41 (1990).

Cohn, et al., "Preparation and Properties of Serum and Plasma Proteins. IV. A System for the Separation into Fractions of the Protein and Lipoprotein Components of Biological Tissues and Fluids," *J. Am. Chem. Soc.* 68: 459–475 (1946).

*Dorland's Illustrated Medical Dictionary* (Twenty–fifth Edition) W.B. Saunders Publishers, 1974.

Emancipator, et al., "In vitro inactivation of bacterial endotoxin by human lipoproteins and apolipoproteins," *Infect Immun* 60(2):596–601 (1992).

Fransechini, et al, "Apolipoprotein AIMilano. Accelerated binding and dissociation from lipids of a human apolipoprotein variant," *J Biol Chem* 260(30):16321–5 (1985).

(List continued on next page.)

Primary Examiner—Christopher S. F. Low
Assistant Examiner—Anish Gupta
(74) Attorney, Agent, or Firm—Holland & Knight LLP

(57) ABSTRACT

The present invention relates to a composition for use in purification of apolipoprotein A (ApoA) or apolipoprotein E (ApoE), said composition comprising a first and a second polymeric material, wherein the first and second polymeric material are immiscible in the primary aqueous solution, and wherein the second polymeric material is amphiphilic and water soluble. The invention further relates to a process for purifying ApoA or ApoE, or variants or mixtures thereof, by first mixing ApoA or ApoE, the composition containing a first and second polymeric material and water. The resulting primary aqueous solution is maintained for a period of time sufficient for essentially separating the phases formed, and removing the phase containing the second polymeric material and the main portion of ApoA or ApoE. Subsequently, the second polymeric material is separated from ApoA or ApoE. The thus produced ApoA or ApoE can be used for the manufacture of a medicament in the treatment of atherosclerosis and cardiovascular diseases, sepsis or peripheral atherosclerosis as well as in a method for treatment of atherosclerosis and cardiovascular diseases, sepsis or peripheral atherosclerosis when administered in a therapeutically effective amount.

4 Claims, No Drawings

OTHER PUBLICATIONS

Fransechini, et al. "Apolipoprotein AIMilano. Disulfide–linked dimers increase high density lipoprotein stability and hinder particle interconversion in carrier plasma," *J Biol Chem* 265(21):1224–31 (1990).

Fransechini, et al. "High density lipoprotein–3 heterogeneity in subjects with the apo–AIMilano variant," *J. Biol. Chem.* 257(17): 9926–30 (1982).

Freudenberg, et al., "Natural Toxins," *Proc. Inc. Symp. Anim., Plant Microb. Toxins*, 6$^{th}$ ed. pp. 349–354.

Index, 11eEd., Merck and Co., Rahway, NJ, pp. 342 and 455 (1989).

Isaachi, et al., "Mature apolipoprotein AI and its precursor proApoAI: influence of the sequence at the 5' end of the gene on the efficiency of expression in *Escherichia coli*," *Gene* 81(1):129–37 (1989).

Karplus, et al., "A new method for reduction of endotoxin contamination from protein solutions," *J Immunol Methods* 105(2):211–20 (1987).

Lerch, et al., "Isolation and Properties of Apolipoprotein A for Therapeutic Use," *Protides Biol. Fluids* 36: 409–416 (1989).

Matsumae, et al., "Specific removal of endotoxin from protein solutions by imobilized histidine," *Biotechnol Appl Biochem* 12(2):129–40 (1990).

Medzour, et al. "Anion–exchange fast protein liquid chromatographic characterization and purification of apolipoproteins A–I, A–II, C–I, C–II, C–III0, C–III1, C–III2 and E from human plasma," *J Chromatogr.* 414(1):35–45 (1987).

Minobe, et al., "Characteristics and applications of adsorbents for pyrogen removal," *Biotechnol Appl Biochem* 10(2):143–53 (1988).

Moguilevsky, et al., "Production of human recombinant proapolipoprotein A–I in *Escherichia coli*: purification and biochemical characterization," *DNA* 8(6):429–36 (1989).

Munford, et al., "Binding of Salmonella typhimurium lipopolysaccharides to rat high–density lipoproteins," *Infect Immun* 34(3):835–43 (1981).

Nilsson, et al., "Immobilization and purification of enzymes with staphylococcal protein A gene fusion vectors," *EMBO J.* 4(4):1075–80 (1985).

Nitschmann, et al., "Vereinfachtes Verfahen zur Gewinnung von humanem Albumin und—Globulin aus Blutplasma mittels Alkoholfallung," *Helv. Chim. Acta*. 37:866–873 (1954).

O'Brien, et al., "Comparison of apolipoprotein and proteoglycan deposits in human coronary atherosclerotic plaques: colocalization of biglycan with apolipoproteins," *Circulation* 98(6):519–27 (1998).

Oncley, et al., "The separation of the Antibodies, Isogglutinins, Prothrombin, Plasminogen and β1—Lipoprotein into Subfractions of Human Plasma," *J. Am. Chem. Soc.* 71: 541–550 (1949).

Peitsch, et al., "A purification method for apolipoprotein A–I and A–II," *Anal Biochem*. 178(2):301–5 (1989).

Pigiet, et al., "Thioredoxin–catalyzed refolding of disulfide––containing proteins," *Proc Natl Acad Sci U S A*. 83(20):7643–7 (1986).

Ross, et al., "Rapid chromatographic purification of apolipoproteins A–I and A–II from human plasma," *Anal Biochem* 149(1):166–8 (1985).

Rubenstein, et al., "A new method for the fractionation of human plasma high density lipoprotein," *Can J Biochem*. 55(7):766–8 (1977).

Segrest, et al., "A molecular theory of lipid–protein interactions in the plasma lipoproteins," *FEBS Lett*. 38(3):247–58 (1974).

Sharma, et al., "Endotoxin detection and elimination in biotechnology," *Biotechnol Appl Biochem*. 8(1):5–22 (1986).

Ulevitch, et al., "New function for high density lipoproteins. Isolation and characterization of a bacterial lipopolysaccharide–high density lipoprotein complex formed in rabbit plasma," *J Clin Invest* 67(3):827–37 (1981).

Walter, et al. Partitioning procedures and techniques: cells, organelles, and membranes, *Methods Enzymol* 228:42–63 (1994).

Weisgraber, et al. "Identification of the disulfide–linked homodimer of apolipoprotein E3 in plasma. Impact on receptor binding activity," *J Biol Chem* 266(18):12029–34 (1991).

Eisenberg et al (1982). *Nature*, vol. 229, pp. 371–374.

Johansson (1974), *Acta Chemica Scandinavica*, vol. 28, pp. 873–882.

Walter et al (1994), *Methods in Enzymology*, vol. 228, pp. 28–42 and 627–640.

Harris et al (1991), *Bioseparation*, vol. 2, pp. 237–246.

Alred et al. (1993), *J. Chromatography*, vol. 628, pp. 205–214.

Alred et al (1992), *Bioseparation*, vol. 2, pp. 363–373.

Alred et al (1994), *J. Chromatography A*, vol. 659, pp. 289–298.

Bradford (1976), *Analytical Biochemistry*, vol. 72, pp. 248–254.

Berggren et al (1995), *J. Chromatography A* vol. 718, pp. 67–79.

Frandeschini et al (1980), *J. Clin. Invewst*, vol. 66, pp. 892–900.

Weisgraber et al (1983), *J. Bio. Chem.*, vol. 258, No. 4, pp. 2508–2513.

Gualandri et al (1985), *Am. J. Hum. Genet.*, vol. 37, pp. 1083–1097.

Nguyen et al (1988), *Appl. Microbiol Biotechnology*, vol. 27, pp. 341–346.

Modlin et al (1974), *J. of Chromatography A*, vol. 668, pp. 229–236.

Galaev et al (1993), *Enzyme Microb. Technol*, vol. 15, pp. 354–366.

Deeb et al (1991), *J. Biological Chemistry*, vol. 266, No. 21, pp. 13654–13660.

Takada et al, (1991), *J. Lipid Research*, vol. 32, pp. 1275–1280.

Matsunaga et al (1991), *Proc. Natl. Acad. Sci. USA*, vol. 88, pp. 2793–2797.

Sirtori et al (1993), Human Apolipoprotein Mutants III, *NATO ASI Series*, vol. II 73, pp. 81–96.

Brewer et al (1978), *Biochemical and Biophysical Research Communications*, vol. 80, No. 3, pp. 623–630.

Weisbrager (1980), *J. Clin. Invest.*, vol. 66, pp. 901–907.

Wiegel et al (1994), *J. Chromatography β*, vol. 661, pp. 159–164.

\* cited by examiner

PROCESS FOR PURIFYING A PROTEIN

This application claims the benefit of Provisional application Ser. No. 60/026,740 filed Sep. 26, 1996.

FIELD OF THE INVENTION

The present invention relates to a composition and process for purifying apolipoprotein A or apolipoprotein E, which are important components of the high density and low density lipoproteins in plasma. More particularly, this invention relates to a composition containing a first and a second polymeric material for use in a process comprising a primary aqueous two-phase separation step followed by separation of ApoA or ApoE from the second polymeric material exhibiting preference for ApoA or ApoE.

BACKGROUND OF THE INVENTION

The main function of lipoproteins in plasma is to transport lipids, such as cholesterol and triglycerides. For transport in plasma, cholesterol, normally as cholesteryl esters, and the triglycerides are included into lipoprotein particles in which they form a hydrophobic core. The core is surrounded by a surface coat containing phospholipids, unesterified cholesterol and proteins called apolipoproteins. The latter are responsible for the lipid transport, and in addition, some may interact with many of the enzymes involved in lipid metabolism. To date, at least nine apolipoproteins have been identified: A-I, A-II, A-IV, B, C-I, C-II, C-III, D and E.

There are four major classes of lipoproteins: chylomicrons (CM), very low density (VLDL), low density (LDL) and high density (HDL) lipoproteins. Of these, HDL is directly involved in the removal of cholesterol from peripheral tissues, carrying it back either to the liver or to other lipoproteins, by a mechanism known as "reverse cholesterol transport" (RCT).

The "protective" role of HDL has been confirmed in a number of studies. Recent studies directed to the protective mechanism(s) of HDL have been focused on apolipoprotein A-I (ApoA-I), the major component of HDL. High plasma levels of ApoA-I are associated with a reduced risk of CHD and presence of coronary lesions.

The apolipoprotein A-IMilano (ApoA-IM) is the first described molecular variant of human ApoA-I (Franceschini et al. (1980) J. Clin. Invest. 66: 892–900). It is characterized by the substitution of Arg 173 with Cys 173 (Weisgraber et al. (1983) J. Biol. Chem. 258: 2508–2513). The mutant apolipoprotein is transmitted as an autosomal dominant trait and 8 generations of carriers have been identified (Gualandri et al. (1984) Am. J. Hum. Genet. 37: 1083–1097). The status of a ApoA-IM carrier individual is characterized by a remarkable reduction in HDL-cholesterol level. In spite of this, the affected subjects do not apparently show any increased risk of arterial disease. Indeed, by examination of the genealogical tree it appears that these subjects may be "protected" from atherosclerosis.

To make possible production of sufficient quantities of ApoA-I in general, and more specifically ApoA-IM, use is made of recombinant DNA techniques, e.g. in E. coli. Thus, recombinant preparation and use of ApoA-IM, monomers as well as dimers, are disclosed in patent specifications WO-A-88/03166 assigned to Farmitalia Carlo Erba (FICE), WO-A-90/12879 assigned to Sirtori et al, as well as WO-A-93/12143 and WO-A-94/13819 both assigned to Pharmacia AB (formerly Kabi Pharmacia AB).

Apo A-IM is a protein containing at least six major α-helix segments and with a very dense structure. Several of the α-helices are amphiphilic, creating an amphiphilic protein where one surface is hydrophobic and the other is hydrophilic (D. Eisenberg et al, Nature, vol. 299 (1982), pp. 371–374). The amphiphilic properties of ApoA-IM and other ApoAs create a tendency to form micellar structures with other proteins and lipids in aqueous solutions.

Apolipoprotein E (ApoE) is a ligand for the LDL receptor. As a result, ApoE plays an important role in cholesterol metabolism. In addition, ApoE is involved in the hepatic clearance of chylomicron remnants.

Several methods have been proposed for purifying ApoA and ApoE, either from plasma or produced by recombinant DNA techniques. On a laboratory scale use is commonly made of centrifugation, ion-exchange chromatography, affinity chromatography, isoelectric focusing, gel filtration and high-performance liquid chromatography (HPLC) (see Methods in Enzymology, vol. 128, Academic Press, San Diego, Calif., USA (1986)). There is, however, a need for additional methods suitable for purification of ApoA and ApoE, especially on an industrial or pilot-plant scale. Such methods would increase the number of process techniques available to optimize the overall purification of ApoA and ApoE.

Aqueous two-phase systems have widespread use in biochemistry and biotechnology for purifying biological materials such as cells, proteins, nucleic acids and steroids (see e.g. P.-Å Albertsson, Partition of cell particles and macromolecules, 3rd ed., Wiley, New York City, N.Y., USA (1986) and H. Walter et al, Partitioning in Aqueous Two-Phase Systems, Academic Press, Orlando, Fla., USA (1985)). The systems are suitable for biological materials because each phase contains about 70 to 90% by weight of water, thereby substantially reducing the risk of denaturation of biomolecules such as proteins (H. Walter et al, Aqueous two-phase systems, Methods in Enzymology, vol. 228, Academic Press, San Diego, Calif., USA (1994)).

The aqueous two-phase systems are composed of two immiscible polymeric materials or one polymeric material in combination with a high salt concentration. Elevating the concentrations above a certain critical value produces two immiscible aqueous phases in which the polymeric materials or polymeric material and salt are partitioned.

The partitioning of proteins in aqueous two-phase systems mainly depends upon protein hydrophobicity, charge and size. The partitioning can be influenced by changing polymeric materials, the molecular weight of the polymeric materials, the pH and by adding salts to the system (G. Johansson, Acta Chem. Scand., B 28 (1974), pp. 873–882).

Aqueous two-phase systems can be scaled up readily, since the partitioning of biological materials such as proteins is essentially independent of the size of the system. The time for phase separation can, however, be prolonged in large-scale systems depending e.g. on the geometry of the separation vessel.

On a laboratory scale, use is commonly made of dextran and polyethylene glycol (PEG) as the immiscible polymeric materials. Dextran is, however, a relatively expensive polymeric material and for large-scale purification, e.g. industrial scale enzyme extraction, various combinations of PEG and salts are more frequent (K. Köhler et al, Methods in Enzymology, vol. 228, Academic Press, Orlando, Fla., USA, (1994), pp. 627–640).

U.S. Pat. No. 4,740,304 to Perstorp AB relates to compositions containing hydroxyalkyl starch for use in systems with two or more phases for extraction, purification, concentration and/or separation of biological substances. In one preferred embodiment, the hydroxyalkyl starch is hydroxypropyl starch (LIPS). In another preferred embodiment the hydroxyalkyl starch is combined with another polymer, e.g. polyethylene glycol (PEG) or polypropylene glycol. In the examples of U.S. Pat. No. 4,740,304, use is made of various enzymes.

The use of aqueous two-phase systems for purifying biomolecules has been limited, however, since the target products have been contaminated with a phase-system polymer, thus necessitating additional and complicated purification steps. Thus, hitherto the target products to be purified have been partitioned to a salt solution or remained dissolved together with a phase-system polymer. To alleviate this problem, the use of thermo-separating polymeric materials in aqueous two-phase systems has been introduced. This makes it possible to perform temperature-induced phase separation whereby the target biomolecule can be separated from the polymeric material in a very efficient way. This technique has been utilized on a laboratory scale for purifying various enzymes. Thus, temperature-induced phase separation has been used to purify 3-phosphoglycerate kinase and hexokinase from baker's yeast homogenate (P. A. Harris et al, Bioseparation, vol. 2 (1991) pp. 237–246). Furthermore, temperature-induced phase separation has been used to purify two ecdysteroids and glucose-6-phosphate dehydrogenase (P. A. Alred et al, J. Chromatogr., vol. 628 (1993) pp. 205–214 and P. A. Alred et al, Bioseparation, vol. 2 (1992), pp. 363–373, respectively). P. A. Alred et al, J. Chromatogr. A, 659 (1994) pp. 289–298, also discloses temperature-induced phase separation for purifying glucose-6-phosphate dehydrogenase, hexokinase and 3-phosphoglycerate kinase from baker's yeast.

EP-A-262651 to Union Carbide relates to a method for recovering enzymes from aqueous solutions which contains at least one polymeric material exhibiting inverse solubility characteristics. The method comprises elevating the temperature of the solution above the temperature of precipitation of the polymeric material and separating the polymeric precipitate from the enzyme-containing solution. The polymeric material is preferably selected from polyalkylene glycols, such as polyethylene or polypropylene glycol, poly (oxyalkylene) polymers or copolymers, ethoxylated surfactants, silicone-modified polyethers and polyvinyl pyrrolidone. The temperature is suitably elevated to a temperature less than about 90° C., preferably between about 50° C. and about 75° C. In the examples of EP-A-262651, use is made of λ-amylase.

Wiegel et al relates to partitioning of high-density lipoproteins (HDL) in two-phase systems (J. Chromatogr. B, 661 (1994) pp. 159–164). Here use is made of dextran and PEG for separating the HDL particles. The preferred enrichment of HDL particles in the dextran-rich more hydrophilic bottom phase is attributed to hydrogen bonding between dextran and the molecules constituting the HDL particles (the apo-protein of HDL).

There are presently several methods known for purifying ApoA and ApoE. There is, however, a need for an additional quick, sensitive and reliable method for preparation of ApoA and ApoE on a pilot-plant and industrial scale. It is the purpose of the present invention to provide such a method.

SUMMARY OF THE INVENTION

The present invention relates to a composition for use in purification of apolipoprotein A (ApoA) or apolipoprotein E (ApoE), said composition comprising a first and a second polymeric material, wherein the first and second polymeric material are immiscible in the primary aqueous solution, and wherein the second polymeric material is amphiphilic and water soluble. The invention further relates to a process for purifying ApoA or ApoE, or variants or mixtures thereof, by first mixing ApoA or ApoE, the composition containing a first and second polymeric material and water. The resulting primary aqueous solution is maintained for a period of time sufficient for essentially separating the phases formed, and removing the phase containing the second polymeric material and the main portion of ApoA or ApoE. Subsequently, the second polymeric material is separated from ApoA or ApoE. The thus produced ApoA or ApoE can be used for the manufacture of a medicament in the treatment of atherosclerosis and cardiovascular diseases, sepsis or peripheral atherosclerosis as well as in a method for treatment of atherosclerosis and cardiovascular diseases, sepsis or peripheral atherosclerosis when administered in a therapeutically effective amount.

DETAILED DESCRIPTION OF THE INVENTION

An object of the present invention is to provide an efficient purifying process for producing ApoA or ApoE with a low enough content of impurities to obviate the need for further purifying steps.

A further object of the present invention is a process providing a high yield of ApoA or ApoE, i.e. a process with a minimal loss of product.

Another object of the present invention is to provide an efficient process, where the biological activity of ApoA or ApoE is essentially retained.

The objects above are met by the present invention, which relates to a composition for use in a primary aqueous solution for purifying apolipoprotein A (ApoA) or apolipoprotein E (ApoE), or variants or mixtures thereof, said composition comprising a first and a second polymeric material, said first and second polymeric material being immiscible in the primary aqueous solution, and said second polymeric material being amphiphilic and water soluble.

The present invention further relates to process for purifying apolipoprotein A (ApoA) or apolipoprotein E (ApoE), or variants or mixtures thereof, by mixing, in arbitrary order, ApoA or ApoE, the composition according to the present invention and water, maintaining the resulting primary aqueous solution for a period of time sufficient for essentially separating the phases formed, removing the phase containing the second polymeric material and the main portion of ApoA or ApoE, and thereafter separating the second polymeric material from ApoA or ApoE.

A preferred embodiment of the present invention, relates to a process for purifying apolipoprotein A (ApoA) or apolipoprotein E (ApoE), or variants or mixtures thereof, by mixing ApoA or ApoE with water and the first and second polymeric material, the second polymeric material exhibiting preference for ApoA or ApoE and inverse solubility characteristics, maintaining the resulting primary aqueous solution for a period of time sufficient for essentially separating the phases formed, and removing the phase containing the second polymeric material and the main portion of ApoA or ApoE. Subsequently, ApoA or ApoE are separated from the second polymeric material by heating the removed phase to a temperature below the temperature where degradation of the ApoA or ApoE occur but above the cloud point of the second polymeric material for precipitating said second polymeric material, and thereafter separating the phase containing the precipitated second polymeric material from the phase containing ApoA or ApoE.

Aqueous two-phase separation followed by separation of the second polymeric material from ApoA or ApoE provides another dimension for purifying ApoA and ApoE, since additional separation criteria are utilized compared to those already used. Thus, quite surprisingly a substantial amount of impurities precipitate in the primary two-phase separation step, while ApoA or ApoE remain essentially dissolved. In particular, the inventors of the present invention have found that aqueous two-phase separation in combination with temperature-induced phase separation can be used efficiently to purify lipoproteins such as ApoA and ApoE.

The present invention also relates to use of a composition for purifying apolipoprotein A (ApoA) or apolipoprotein E (ApoE), or variants or mixtures thereof, in a primary aqueous solution, wherein said composition comprises a first and a second polymeric material, said first and second polymeric material being immiscible in the primary aqueous solution, and said second polymeric material being amphiphilic and water soluble.

The present invention further relates to use of ApoA or ApoE produced according to the inventive process for the manufacture of a medicament comprising the ApoA or ApoE in the treatment of atherosclerosis and cardiovascular diseases, sepsis or peripheral atherosclerosis.

The present invention further relates to a method for treatment of atherosclerosis and cardiovascular diseases, sepsis or peripheral atherosclerosis by administering ApoA or ApoE produced according to the inventive process in a therapeutically effective amount.

The two polymeric materials used in the primary aqueous two phase separation must be immiscible. Therefore, one polymeric material should be essentially hydrophilic and the other more hydrophobic but still water soluble, i.e. amphiphilic. Also, the concentrations of the first and second polymeric material should be high enough to bring about a phase separation into at least two phases. Examples of hydrophilic, first polymeric materials suitable for use in the present invention include hydroxyalkyl cellulose, hydroxyalkyl starches, starch, dextran, pullulan, and derivatives and mixtures thereof. Pullulan is a microbial polysaccharide previously employed for purifying enzymes in aqueous two-phase systems (Nguyen et al, Appl. Microbiol. Biotechnol., vol. 27 (1988) pp. 341–346). The hydroxyalkyl starches are suitably selected from the group consisting of hydroxymethyl starch, hydroxyethyl starch, hydroxypropyl starch and hydroxybutyl starch, and mixtures thereof. The molecular weight of the hydrophilic, first polymeric material can be in the range of from about 10,000 up to about 5,000,000 Da, suitably in the range of from 40,000 up to 500,000 Da, and preferably in the range of from 100,000 up to 300,000 Da. Specific examples of hydroxyalkyl starches suitable for use in the present invention include Reppal PES 100 and Reppal PES 200, both of which are hydroxypropyl starches marketed by Carbamyl AB of Kristianstad, Sweden. The average molecular weight of Reppal PES 100 and Reppal PES 200 are 100,000 Da and 200,000 Da, respectively.

As stated in the previous paragraph, the second polymeric material shall be amphiphilic and water soluble. In the present invention, the amphiphilic second polymeric material shall interact with the target proteins ApoA or ApoE. In this way, ApoA or ApoE will be extracted into the more hydrophobic phase and thereby separated from more hydrophilic contaminants such as bulk proteins commonly encountered in plasma and crude or partly purified solutions/cell broths from recombinant DNA processes. Examples of such contaminants are proteins from E. coli. In the experiments disclosed in Example 1 of the present application, the amphiphilic copolymer was partitioned mainly to the top phase. Therefore, in these experiments the main portion of ApoA or ApoE was distributed to the copolymer-rich top phase.

In the present invention, the second polymeric material preferably exhibits inverse solubility. The term "inverse solubility" means that the solubility of the polymeric material varies inversely with the solution temperature. This means that the solubility of the polymeric material decreases with increasing solution temperature. Inverse solubility is therefore directly opposed to the temperature effect exhibited by most solutes.

Compositions containing three or more polymeric materials are also within the scope of the present invention. Thus, multi-phase separation can be obtained by selecting suitable combinations of three or more polymeric materials and sufficiently high concentrations thereof in the primary aqueous solution. The polymeric materials should be chosen such that the solubility of ApoA or ApoE is much higher in one polymer phase than in the others.

In the present invention, the term "primary aqueous solution" relates to the initial separation step before separation into at least two phases, unless otherwise stated.

The primary solution is aqueous, i.e. the main portion of the solvent is water. The water can be added separately or together with any of the components necessary for the primary separation step. Thus, one or more aqueous solutions containing ApoA or ApoE, the first or second polymeric material, can be used to introduce the component per se as well as the water required to make up the primary aqueous solution.

The concentration of the target protein in the primary aqueous solution can be in the range of from about 0.1 g/l up to about 50 g/l of the primary aqueous solution, suitably within the range of from 0.5 up to 20 g/l, and preferably within the range of from 1 up to 10 g/l.

The concentration of the hydrophilic, first polymeric material in the primary aqueous solution can be in the range of from about 1 up to about 30% by weight of the total weight of the primary aqueous solution, suitably within the range of from 3 up to 20% by weight, and preferably within the range of from 5 up to 15% by weight.

In the primary aqueous solution, the concentration of the amphiphilic, second polymeric material can be in the range of from about 0.5 up to about 30% by weight of the total weight of the aqueous solution, suitably within the range of from 3 up to 20% by weight, and preferably within the range of from 5 up to 15% by weight.

In the primary aqueous solution, the ratio between the concentration of the target protein and the amphiphilic, second polymeric material can be in the range of from about 3:1 to about 1:2,500 calculated by weight, suitably within the range of from 2:3 to 1:400 by weight, and preferably within the range of from 1:3 to 1:150 by weight.

In the primary aqueous solution, the ratio between the concentration of the hydrophilic, first polymeric material and the amphiphilic, second polymeric material can be in the range of from about 20:1 to about 1:10 calculated by weight, suitably within the range from 10:1 to 1:5 by weight, and preferably within the range of from 5:1 to 1:2 by weight.

After mixing ApoA or ApoE with the first and second polymeric material, the primary aqueous solution is maintained for a period of time sufficient for essentially separating the at least two phases formed. This period of time can be in the range of from about 2 min up to about 5 hours, suitably in the range of from 5 min up to 2 hours and preferably in the range of from 10 min up to 1 hour. However, the period of time required for phase separation can be reduced by using e.g. centrifugal separation, centrifugal centrifugation or centrifugal decanting, before allowing the primary aqueous solution to separate into the at least two phases. If such means are employed, the period of time for the separation into at least two phases can be in the range of from about 5 sec up to about 60 min, and suitably in the range of from 10 sec up to 30 min.

The temperature of the primary aqueous solution suitably lies in the range of from about 5 up to about 40° C., and preferably in the range of from 15 up to 30° C.

In a preferred embodiment of the present invention, a compound containing two or three nitrogen atoms bonded to a carbon atom is present in the primary aqueous solution. In this way, an improved purification and yield can be obtained, since the protein more readily partitions to the more hydrophobic phase. The advantageous effect obtained with such nitrogen-containing compounds is quite surprising, since compounds such as urea are conventionally used to denature proteins. Suitable examples of such nitrogen-containing compounds are urea, arginine, guanidine hydrochloride, benzamidine and mixtures thereof. Use of urea is particularly preferred, due to increased solubility of ApoA or ApoE and decreased formation of aggregates of ApoA or ApoE. If used, the concentration of the compound containing two or three nitrogen atoms bonded to a carbon atom should be in the range of from about 0.5 M up to saturation, suitably in the range of from 1 M up to 8 M, and preferably in the range of from 1.5 M up to 6 M.

In the primary aqueous solution, the ratio between the target protein and the nitrogen-containing compound can be in the range of from about 1:1 to about 1:5,000 calculated by weight, suitably within the range of from 1:4 to 1:700 by weight, and preferably within the range of from 1:6 to 1:250 by weight.

The partitioning of ApoA and ApoE to the hydrophobic phase can be enhanced by adding a compound with a hydrophobic cation to the primary aqueous solution. Suitable compounds include inorganic salts containing cations such as straight or branched trimethyl ammonium, triethyl ammonium, tripropyl ammonium, tributyl ammonium, tetramethyl ammonium, tetraethyl ammonium, tetrapropyl ammonium, and tetrabutyl ammonium, and anions such as phosphates, sulfate, nitrate, chloride, and hydrogen carbonate. A specific example is triethyl ammonium phosphate. The concentration of a compound with a hydrophobic cation should be selected to give an enhanced partitioning effect, while at the same time avoiding precipitation of ApoA or ApoE. Determination of the range of suitable concentrations for each particular compound lies within the competence of the person skilled in the art.

The partitioning of molecules between the phases of two-phase systems is described by the partitioning coefficient K. It is defined as $$K = C_T/C_B \qquad (1)$$

wherein $C_T$=the concentration in the top phase of the molecule of interest $C_B$=the concentration in the bottom phase of the molecule of interest.

The partitioning of molecules between the phases of two-phase systems can be shown in phase diagrams. Here, the border line between one and two phases is called the binodial curve. The polymer concentration of the two phases in equilibrium with each other are described by tie lines in the phase diagram. Increasing the polymer concentration, i.e. increasing the tie line length, leads to more extreme partitioning in two-phase systems (G. Johansson, Methods in Enzymology, vol. 228 (1994) pp. 28–42). It lies within the competence of the person skilled in the art to perform experiments for arriving at conditions for suitable partitioning between the two phases.

Two suitable combinations of a hydrophilic, first polymeric material and an amphiphilic, second polymeric material for use in the present invention are Reppal PES 200 in combination with UCON 50-HB-5100 and Reppal PES 200 in combination with $EO_{30}PO_{70}$. Phase diagrams showing the partitioning between the two phases in these systems are given in P. A. Alred et al, Journal of Chromatography, 659 (1994) pp. 289–298, and R. F. Modlin et al, Journal of Chromatography, 668 (1994) pp. 229–236, respectively.

After the primary two-phase separation, the aqueous phase containing the second polymeric material and the main portion of ApoA or ApoE is removed. The second polymeric material is thereafter separated from ApoA or ApoE, e.g. by chromatography, such as affinity or ion-exchange chromatography, or by solvent extraction. It is also conceivable to use yet another two-phase system containing a third polymeric material or a salt, suitably an inorganic salt, for separating the second polymeric material from ApoA or ApoE. In a particularly preferred embodiment, however, the second polymeric material exhibits inverse solubility characteristics and the aqueous phase containing the second polymeric material and the main portion of ApoA or ApoE is brought to a separation vessel for further processing.

Although various methods are available for separating the second polymeric material from ApoA or ApoE as is evident from the previous paragraph, the present invention will in the following be described in more detail with reference to temperature-induced phase separation with a second polymeric material exhibiting inverse solubility characteristics.

In the particularly preferred embodiment, temperature-induced phase separation is performed by heating the phase containing the main portion of ApoA or ApoE to a temperature above the cloud point of the second polymeric material exhibiting inverse solubility but below the temperature where degradation of the ApoA or ApoE occur. The cloud point or phase separation temperature is a characteristic feature of polymeric materials exhibiting inverse solubility. Thus, by raising the temperature of a solution containing such a polymeric material above the cloud point, the solution becomes cloudy, owing to separation into two phases and precipitation of the polymeric material exhibiting inverse solubility. A second phase separation is hereby obtained, where a polymer-rich and a water-rich phase are formed. The water-rich phase is almost free of polymer, i.e. it commonly contains less than 1% of polymer. Conventionally, also, the polymer-rich phase forms the bottom phase after heating, since the density of the polymer-rich phase is normally higher than that of the water-rich phase. The densities can, however, be reversed by various manipulations, e.g. addition of chemicals such as urea in sufficient quantities. In the present invention, the ApoA or ApoE are almost exclusively partitioned to the water-rich phase, thereby reducing the necessity for further purification of the protein at issue.

To make possible technical and economical use of polymeric materials exhibiting inverse solubility, the cloud point must be above the freezing-point of the solution and lower than 100° C. In the present invention, the cloud point of the second polymeric material exhibiting inverse solubility can be in the range of from about 5 up to about 90° C., suitably in the range of from 10 up to 75° C. Preferably, the cloud point of the second polymeric material exhibiting inverse solubility lies in the range of from 15 up to 60° C., more preferably in the range of from 20 up to 40° C.

The temperature to which the phase containing the second polymeric material must be elevated in the temperature-induced phase separation can be reduced by selecting a second polymeric material with a suitably low cloud point as is evident from the previous paragraph. However, the temperature to which the phase containing the second polymeric material must be elevated to bring about precipitation of the second polymeric material can be reduced also by adding a small amount of an organic or more commonly inorganic salt to said phase. Thus, the cloud point of UCON 50-HB-5100 being 50° C. in the absence of salt, can be lowered to e.g. 37° C. by addition of salt. It is, however, preferred that the temperature-induced phase separation is carried out in the essential absence of salt, since this facilitates the subsequent purification of ApoA or ApoE.

Polymeric materials exhibiting inverse solubility and suitable for use in the present invention as the second polymeric material can be found in I. Y. Galaev et al, Enzyme Microb. Tech., vol. 15 (1993), pp. 354–366, which is hereby incorporated by reference. Specifically, polymeric materials exhibiting inverse solubility and suitable for use in the present invention as the second polymeric material include polyalkylene glycols, poly(oxyalkylene) polymers, poly(oxyalkylene) copolymers, polyvinyl pyrrolidone, polyvinyl alcohol, polyvinyl caprolactam, polyvinyl methylether, alkoxylated surfactants, alkoxylated starches, alkoxylated cellulose, alkyl hydroxyalkyl cellulose, silicone-modified polyethers, and derivatives and mixtures thereof. Suitable polyalkylene glycols include polyethylene glycol, polypropylene glycol, and derivatives thereof, such as acrylic and methacrylic substituted polyethylene and polypropylene glycol. Suitable alkoxylated surfactants, starches, and cellulose, include methoxylated and ethoxylated surfactants, starches, and cellulose. Suitable alkyl hydroxyalkyl celluloses include those celluloses where the alkyl groups have from 1 up to 4 carbon atoms. A preferred alkyl hydroxyalkyl cellulose is ethyl hydroxyethyl cellulose (EHEC). Suitable poly(oxyalkylene) copolymers include random and block copolymers of ethylene oxide and propylene oxide. The hydrophobicity of the copolymers of ethylene oxide and propylene oxide increases with increasing propylene oxide content. The content of propylene oxide in the copolymer of ethylene oxide and propylene oxide suitably lies in the range of from about 30 up to about 90% by weight of the total weight of the copolymer, preferably within the range of from 40 up to 80% by weight. A specific example of a copolymer of ethylene oxide and propylene oxide suitable for use in the present invention is UCON 50-HB-5100 marketed by Union Carbide, Corp., New York City, N.Y., USA. UCON 50-HB-5100 is a random linear, non-ionic copolymer composed of 50% by weight of ethylene oxide and 50% by weight of propylene oxide, with a molecular weight ($M_r$) of 4,000 Da and a cloud point of 50° C. Another specific example of a a random copolymer composed of 50% by weight of ethylene oxide and 50% by weight of propylene oxide is Breox PAG 50A 1000 marketed by International Speciality Chemicals Ltd. of Southampton, England. Breox PAG 50A 1000 has a molecular weight ($M_r$) of 3,900 Da and a cloud point of 50° C. Another example of a copolymer of ethylene oxide and propylene oxide suitable for use in the present invention is $EO_{30}PO_{70}$ which is a random copolymer composed of 30% by weight of ethylene oxide and 70% by weight of propylene oxide, with a molecular weight ($M_r$) of 3,200 Da and a cloud point of 38° C. Yet another suitable example is $EO_{20}PO_{80}$ which is a random copolymer composed of 20% by weight of ethylene oxide and 80% by weight of propylene oxide, with a molecular weight ($M_r$) of 3,300 Da and a cloud point of 25° C. in an aqueous solution containing 10% by weight of the copolymer. $EO_{30}PO_{70}$ and $EO_{20}PO_{80}$ are marketed by Shearwater Polymers, Inc., Huntsville, Ala., USA.

The Japanese patent specification with publication number JP 1994-228319 to Hidetoshi Tsuchida, discloses further polymeric materials exhibiting inverse solubility. The polymeric materials comprise block copolymers of propylene oxide and another water-soluble polymer with a molecular weight exceeding 30,000 Da. The entire content of JP 1994-228319 is hereby incorporated by reference in the present application.

The concentration of the target protein in the second aqueous solution can be in the range of from about 0.1 up to about 50 g/l of the second aqueous solution, suitably within the range of from 0.5 up to 20 g/l, and preferably within the range of from 1 up to 10 g/l.

In the temperature-induced phase separation step, the hydrophobic phase from the primary aqueous separation step is maintained for a period of time sufficient for essentially separating ApoA or ApoE from the second polymeric material. This period of time can be in the range of from about 60 sec up to about 5 hours, suitably in the range of from 5 min up to 1 hour and preferably in the range of from 10 min up to 30 min. However, the period of time required for phase separation can be reduced by using e.g. centrifugal separation, centrifugal centrifugation or centrifugal decanting, before allowing ApoA or ApoE to separate from the second polymeric material. If such means are employed, the period of time for separation can be in the range of from about 5 sec up to about 60 min, and suitably in the range of from 10 sec up to 30 min.

The present process can be continuous, e.g. performed on a column, or batch-wise.

The present invention is advantageously used for purifying any apolipoprotein A (ApoA) or Apolipoprotein E (ApoE), or variants or mixtures thereof.

The present invention can be applied to ApoA or ApoE obtained from plasma, suitably human plasma, or produced by a recombinant DNA technique, suitably in gram-negative bacteria, and preferably in *E. coli*. The ApoA or ApoE can be unpurified, or essentially unpurified, or it can be pretreated before applying the present invention. Examples of pretreatment are diafiltration and ultrafiltration.

In the present invention, the terms ApoA and ApoE include any preform or fragment, or any truncated, extended or mutated form, or any mixture of any of these forms or fragments. Preform relates e.g. to the 249 amino acid Met form of ApoA-I as disclosed in WO-A-88/03166 assigned to Sirtori et al. Other preforms are the proapolipoprotein A-I's disclosed in U.S. Pat. No. 5,059,528 to UCB as well as EP-A-308336, JP 216988/1984 and JP 252048/1987 all to Mitsubishi Chem. Ind. Fragment relates to a part of ApoA or ApoE containing at least one α-helix, e.g. as disclosed in WO-A-93/25581 assigned to Innogenetics S.A. of Belgium. Truncated and extended forms relate to ApoA and ApoE molecules where one or more amino acids are missing or has been added, respectively, at the N and/or C terminal ends of the molecules. Suitably, from two up to eight amino acids are missing or have been added, preferably from three up to six amino acids. Mutated forms relate to ApoA and ApoE molecules where one or more amino acid has been substituted by another amino acid, e.g. ApoA-IM as disclosed in WO-A-93/12143 and WO-A-94/13819. Other mutated forms are ApoA-ISeattle (Deeb et al (1991) J. Bio. Chem. 266:13654–13660), ApoA-IYame (Takada et al (1991) J. Lipid Res. 32: 1275 ff) and a yet unnamed mutated form of ApoA-I (Matsunaga et al (1991) Proc. Natl. Acad. Sci. USA 88:2793–2797).

Human ApoE and variants thereof, are disclosed in "Human Apolipo-protein Mutants III", ed. by C. R. Sirtori et al (1993) Nato ASI Series, Springer Verlag, Berlin, 11 73:81–96.

The present invention can be used to advantage for purifying ApoA as well as ApoE. In the following description, however, use will be made of ApoA to further describe the present invention.

Known ApoA's are e.g. ApoA-I, ApoA-II and ApoA-IV. In the present invention, suitably, the ApoA is ApoA-I, or variants or mixtures thereof. Natural plasma ApoA-I is a single polypeptide chain of 243 amino acids, whose primary sequence is known (Brewer et al. (1978) Biochem. Biophys. Res. Commun. 80: 623–630). More suitably, the ApoA is a mutated form of ApoA-I where at least one Cys residue has been substituted for an amino acid residue, preferably an Arg residue, making formation of disulfide-linked dimer possible. In the amino acid sequence of natural human ApoA-I, Arg residues are located at positions 10, 27, 61, 83, 116, 123, 131, 149, 151, 153, 160, 171, 173, 177, 188 and 215. Of these, substitutions are preferred at one or more of positions 160, 171, 173, 177 and 188, i.e. at positions within the same α-helix. More preferably, the Arg residue is substituted at positions 171 and/or 173. Most preferably, the ApoA-I is ApoA-IM.

Human apolipoprotein A-IMilano (ApoA-IM) is a naturally occurring mutated form of normal ApoA-I (Weisgraber et al. (1980) J. Clin. Invest. 66: 901–907). In ApoA-IM, one residue of the amino acid arginine (Arg 173) has been replaced by a residue of the amino acid cysteine (Cys 173). Since ApoA-IM contains one cysteine residue per polypeptide chain, it may exist as a monomer or as a disulfide-linked dimer. The molecular weight of the monomer is about 28,000 Da and for the dimer about 56,000 Da. These two forms are chemically interchangeable, and the term ApoA-IM does not, in the present context, discriminate between the two forms.

The following Examples are provided for purposes of illustration only and are not to be construed as in any way limiting the scope of the present invention, which is defined by the appended claims.

The percentages and parts are per weight, unless otherwise stated.

Experimental

Materials

Recombinant apolipoprotein A-IM was produced in *E. coli* by Pharmacia AB in Stockholm, Sweden. The cells were separated and the filtrate was concentrated 10 times by ultrafiltration using a membrane with a 10,000 Da cut-off. The concentration of Apo A-IM after ultrafiltration was 2.8 mg/ml. Partly purified ApoA-IM in 20 mM phosphate buffer, pH=7 was used as starting material in all performed tests.

The polymers in the bottom phase were two hydroxypropyl starch polymers from Lyckeby Reppe AB of Växjö, Sweden. Reppal PES 100 had a molecular weight ($M_r$) of 100,000 and Reppal PES 200 had a molecular weight ($M_r$) of 200,000.

The top-phase polymers were $EO_{30}PO_{70}$ ($M_r$ 3,200) and $EO_{20}PO_{80}$ ($M_r$ 3,300) from Shearwater Polymers, Inc., Huntsville, Ala., USA.

All of the chemicals were of analytical reagent grade.

Analytical Methods and Calculations

The total protein content was determined according to Bradford, Anal. Biochem., vol. 72 (1976) pp. 248–254, using Coomassie Brilliant Blue G. The absorption was measured at 595 and 465 nm and the absorption obtained at 465 nm was then subtracted from the absorption obtained at 595 nm. Bovine serum albumin was used as standard.

The yield was calculated as:

$$\text{Yield}=(C^t_{Apo}*V^t)/(C_{Apo}*V)\times 100 \qquad (2)$$

wherein $C^t_{Apo}$=concentration of Apo A-$1_M$ in the top phase $C_{Apo}$=concentration of Apo A-$1_M$ in the starting material $V^t$=volume of the top phase and V=volume of material put into the system The degree of purification of Apo A-1M in the systems was calculated as:

$$\text{Degree of purification}=(C^t_{Apo}/C^t)/(C_{Apo}/C) \qquad (3)$$

wherein $C^t_{Apo}$=concentration of Apo A-$1_M$ in the top phase $C_{Apo}$=concentration of Apo A-$1_M$ in the starting material $C^t$=total protein concentration in the top phase and C=total protein concentration in the starting material.

The polymer concentrations were calculated as % weight/weight (w/w).

The experiments were performed in duplicate and the experimental data given are average values.

EXAMPLE 1

The effect on purification and yield of primary aqueous two-phase separation followed by temperature-induced phase separation according to the present invention was studied using Apo A-IM as target protein. After cell removal, an *E. coli* fermentation solution containing Apo A-IM was added to an aqueous solution containing Reppal PES 100, $EO_{30}PO_{70}$ and urea. The resulting primary aqueous solution containing 17% Reppal PES 100, 12% $EO_{30}PO_{70}$ and 3.5 M urea was mixed with a magnetic stirrer. The temperature in the primary aqueous solution was 20° C. The separation into two phases was enhanced by centrifuging at 1,360 g for 10 min. After phase separation in the primary aqueous system, temperature-induced phase separation was performed by maintaining the isolated top phase at 50° C. for 30 min.

When analyzing the polymer phase on SDS-PAGE, and staining the gel with silver nitrate, no protein bands were observed.

The degree of purification and yield of Apo A-IM in the primary top phase and the temperature-induced top phase are evident from Table I. The degree of purification and yield were calculated according to formulas (2) and (3) based on ELISA results.

TABLE I

Purification of Apo A-1M according to the present invention.

| | Apo A-IM conc. (g/l) | Total protein conc. (g/l) | Yield (%) | Degree of purification |
|---|---|---|---|---|
| Starting material | 0.67 | 6.0 | (100) | (1) |
| Primary top phase | 0.60 | 2.0 | 82 | 2.7 |
| Water-rich top phase after thermal separation | 0.75 | 2.2 | 82 | 3.0 |

As is evident from Table I, the yield was 82% with a degree of purification of 2.7 after the primary step. No loss of Apo A-IM was observed in the subsequent thermal separation step and the purification was slightly increased in this step. A concentration of the proteins was obtained due to the volume reduction in the temperature-induce phase separation.

EXAMPLE 2

The process according to Example 1 was repeated with the difference that the fermentation solution was concentrated after cell removal, and Reppal PES 200 was used as the first polymeric material. The primary aqueous solution contained 21% Reppal PES 200, 10% $EO_{30}PO_{70}$ and 3.0 M urea. The results are shown in Table II.

TABLE II

Purification of Apo A-1M according to the present invention.

| | Apo A-IM conc. (g/l) | Total protein conc. (g/l) | Yield (%) | Degree of purification |
|---|---|---|---|---|
| Starting material | 5.4 | 31.2 | (100) | (1) |
| Primary top phase | 6.5 | 14.0 | 62 | 2.7 |
| Water-rich top phase after thermal separation | 7.4 | 16.1 | 62 | 2.7 |

EXAMPLE 3

The process according to Example 2 was repeated with the difference that $EO_{20}PO_{80}$ was used as the second polymeric material. The results are shown in Table III.

TABLE III

Purification of Apo A-1M according to the present invention.

| | Apo A-IM conc. (g/l) | Total protein conc. (g/l) | Yield (%) | Degree of purification |
|---|---|---|---|---|
| Starting material | 5.4 | 31.2 | (100) | (1) |
| Primary top phase | 4.9 | 9.9 | 61 | 2.9 |
| Water-rich top phase after thermal separation | 5.3 | 11.0 | 60 | 2.8 |

As is evident also from Tables II and III, the yield is in excess of 60% with a degree of purification in excess of 2.7 after the primary step.

What is claimed is:

1. A process for purifying biologically active apolipoprotein A (ApoA) or apolipoprotein E (ApoE), or variants or mixtures thereof the improvement comprising mixing to produce a primary aqueous solution a source of ApoA or ApoE, a compound containing two or three nitrogen atoms bonded to a carbon atom, and a composition comprising a first polymeric material and a second polymeric material, and water, wherein die first and second polymeric materials are immiscible in the prima aqueous solution, and the second polymeric material is amphiphilic and water soluble, maintaining the resulting primary aqueous solution for a period of time sufficient for essentially separating the phases formed, removing a phase containing the second polymeric material and a main portion of ApoA or ApoE, and thereafter separating the second polymeric material from the biologically active ApoA or ApoE.

2. A process according to claim 1, wherein a compound containing two or three nitrogen atoms bonded to a carbon atom is selected from the group consisting of urea, arginine, guanidine hydrochloride, benzamidine and mixtures thereof.

3. A process according to claim 1, wherein the concentration of the compound containing two or three nitrogen atoms bonded to a carbon atom lies in the range of from about 0.5 M up to saturation.

4. A process according to claim 3, wherein the concentration of the compound containing 2 or 3 nitrogen atoms bonded to a carbon atom lies in the range of from 1 M up to 8 M.

* * * * *